(12) United States Patent
Schaeffer et al.

(10) Patent No.: US 7,704,748 B2
(45) Date of Patent: Apr. 27, 2010

(54) GAS ANALYZER FOR MEASURING THE FLAMMABILITY OF MIXTURES OF COMBUSTIBLE GASES AND OXYGEN

(75) Inventors: Christopher G. Schaeffer, Cedar Grove, NJ (US); Matthew James Schaeffer, North Caldwell, NJ (US); Pravin Patel, Parsippany, NJ (US)

(73) Assignee: Control Instruments Corporation, Farifield, NJ (US)

( * ) Notice: Subject to any disclaimer, the term of this patent is extended or adjusted under 35 U.S.C. 154(b) by 1197 days.

(21) Appl. No.: 10/519,313

(22) PCT Filed: Jun. 26, 2003

(86) PCT No.: PCT/US03/20285

§ 371 (c)(1),
(2), (4) Date: Nov. 16, 2005

(87) PCT Pub. No.: WO2004/003533

PCT Pub. Date: Jan. 8, 2004

(65) Prior Publication Data

US 2006/0234387 A1    Oct. 19, 2006

Related U.S. Application Data

(60) Provisional application No. 60/392,338, filed on Jun. 27, 2002.

(51) Int. Cl.
  *G01N 25/28* (2006.01)
(52) U.S. Cl. .............. 436/160; 436/147; 436/155; 436/171; 422/78; 422/82; 422/12; 422/94; 73/25.01

(58) Field of Classification Search .............. 436/47, 436/155, 160, 171; 422/78, 82, 12, 94, 82.12; 73/25.01
See application file for complete search history.

(56) References Cited

U.S. PATENT DOCUMENTS

| | | |
|---|---|---|
| 3,767,363 A | 10/1973 | Hofmann |
| 3,984,205 A | 10/1976 | Karas et al. |
| 4,311,664 A | 1/1982 | Zaremba et al. |
| 4,382,698 A | 5/1983 | Szonntagh |
| 4,397,958 A | 8/1983 | Vroom |
| 4,415,278 A | 11/1983 | Szonntagh |
| 5,053,200 A | 10/1991 | Schaeffer et al. |
| 5,224,776 A | 7/1993 | Clingman, Jr. et al. |
| 5,432,095 A | 7/1995 | Forsberg |
| 5,741,711 A | 4/1998 | Amirav et al. |
| 6,096,178 A | 8/2000 | Amirav et al. |
| 6,485,689 B1 * | 11/2002 | Huang et al. .............. 422/83 |

OTHER PUBLICATIONS

Chapman et al, Analyst, Jul. 1969, vol. 94, 563-568.*

* cited by examiner

*Primary Examiner*—Jan M Ludlow
(74) *Attorney, Agent, or Firm*—Fox Rothschild LLP; Richard C. Woodbridge (57) ABSTRACT

A novel Flame Temperature Analyzer (FTA) method and apparatus for measuring combustible gas concentration and oxygen content in a sample gas includes supplying a mixture of oxidant and fuel to a sensing flame and measuring the temperature of the flame as the sample is added to the combustion chamber.

14 Claims, 8 Drawing Sheets

Figure 4b - FID Type Analyzer

Figure 4c - Improved FTA Analyzer

Figure 6g

| Oxygen Effect and Signal Strength for Various Initial Flame Temperatures | | | | | | | | | | | | |
|---|---|---|---|---|---|---|---|---|---|---|---|---|
| Flame Temperature in 21% Oxygen | 349 | 400 | 449 | 501 | 549 | 599 | 627 | 649 | 702 | 726 | 750 | 776 |
| Reading Shift, %LFL, at 10% Oxygen | 14 | 15 | 13 | 12 | 10 | 5 | 2 | 0 | -10 | -16 | -23 | -31 |
| Loss of Signal Strength | -36% | -18% | -9% | -2% | 0% | -1% | -4% | -6% | -12% | -15% | -19% | -24% |

Figure 7a

Representation of prior art FTA flame with oxygen effect.

Zone A - hot tip of burner where pure hydrogen fuel undergoes preheating.
Zone B - Ignition zone does not occur because no oxygen is present in the hydrogen fuel
Zone C - Inner core of flame consisting of unburned gas
Zone D - main reaction zone where oxygen diffuses inward from the sample to support combustion. Zone D is dependent on rate of oxygen diffusion, which in turn varies as the concentration of oxygen in the sample varies.
Zone E - Products of combustion
Zone G - Zone containing sample, which can have a varying concentration of oxygen.

Figure 7b

Representation of improved FID flame with hydrogen-nitrogen fuel to prevent oxygen dependency.

Zone A - hot tip of burner where mixture of hydrogen, nitrogen and sample undergoes preheating.
Zone B - Ignition zone does not occur because insufficient oxygen is present in the sample-hydrogen-nitrogen mixture
Zone C - Inner core of flame consisting of unburned gas
Zone D - main reaction zone where oxygen diffuses inward to support combustion
Zone E - Products of combustion
Zone F - Oxygen rich zone containing combustion air

Figure 7c

Representation of improved FTA flame with hydrogen-air fuel to prevent oxygen effect.

Zone A - hot tip of burner where mixture of hydrogen, nitrogen and sample undergoes preheating.
Zone B - Ignition zone which always occurs because oxygen is present in the hydrogen-air mixture. This zone stabilizes the flame.
Zone C - Inner core of flame consisting of unburned gas
Zone D - main reaction zone where oxygen diffuses inward from the sample to support combustion
Zone E - Products of combustion
Zone G - Zone containing sample with a varying concentration of oxygen

GAS ANALYZER FOR MEASURING THE FLAMMABILITY OF MIXTURES OF COMBUSTIBLE GASES AND OXYGEN

CROSS REFERENCE TO RELATED APPLICATIONS

The present invention is related to and claims the benefit of PCT Application No. PCT/USO3/20285 filed on Jun. 26, 2003, and U.S. Provisional Patent Application No. 60/392,338 filed on Jun. 27, 2002 by Mathew James Schaeffer and Christopher G. Schaeffer entitled "Gas Analyzer for Measuring the Flammability of Mixtures of Combustible Gases and Oxygen", the contents of both of which are hereby incorporated by reference.

FIELD OF THE INVENTION

The present invention relates to the measurement of combustible gases and oxygen mixtures in atmospheres having the potential for a fire or explosion, and in particular to temperature measurements of diffusion flames within samples of combustible mixtures.

BACKGROUND OF THE INVENTION

Description of Related Art

Measurement of combustibles gases and oxygen in industrial processes can prevent fires and explosions. The National Fire Protection Association NFPA-86 Standard for Ovens and Furnaces (NFPA-86) defines the safety requirements for flammability measurements in industrial processes that use combustible substances, typically solvents, for printing, painting, coating or treating various materials, which are then dried in ovens. For combustible gases, this is achieved by keeping the concentration under the Lower Flammable Limit, or LFL, below which the combustible gas cannot propagate a flame. A margin of safety is often required, so that the limit to an industrial operation is often expressed as a percentage of the LFL, for example 50% LFL. For oxygen, this means keeping the concentration, by a safe margin, under the limiting oxygen concentration, or LOC, below which there is insufficient oxygen for an explosion, for example 3% oxygen below the LOC.

Efforts to reduce emissions of volatile organic compounds (VOCs) from industrial sources have resulted in the widespread use of thermal oxidizers. VOCs that were once released to the atmosphere are now captured and transported to an oxidizer to be destroyed. Since VOCs are combustible, they can form explosive mixtures in air. The thermal oxidizer, as well as the process ductwork which transports the VOCs to the oxidizer, must be protected. The oxidizer is a near-certain source of ignition to an explosive mixture, and the oxidizer's function requires sufficient oxygen to support combustion, so the primary method of protection is to limit the concentration of VOCs to a level safely below the LFL.

Recent improvements in manufacturing techniques have led to increases in throughput, which can mean that higher volumes of combustibles must be handled safely. It is not uncommon for a particular process with a long history of safe operation to experience an incident after a seemingly unrelated change in speed, formulation, or temperature causes an unintentional increase in the concentration of combustibles.

The drive to become energy efficiency focuses on reducing the amount of fuel used for heating, which is sometimes achieved by reducing ventilation, and in so doing, results in higher concentrations of combustibles. The need to measure flammability accurately under a wide range of conditions is more important than ever.

Process conditions can vary widely. The types of combustible gases and their proportions, the oxygen concentration, water vapor content, and other gases in the process might be unpredictable, or may vary over a wide range. The conditions during normal operation might be well defined, but under a potentially hazardous process upset, these conditions may be significantly different than what was originally anticipated. An analyzer capable of giving a reliable alarm under the widest range of potential circumstances is needed.

For example, a kiln in which ceramics are fired have rarely experienced problems in the past, but now kilns may have more complex parts with greater surface areas, using shorter cycle times, and more volatile binders. The concentration of combustibles can now reach very high concentrations. Furthermore, the process can generate an extremely wide range of combustible vapors—many different hydrocarbon species of varying molecular weights, plus hydrogen or carbon monoxide, depending upon the kiln conditions at the time the vapors are generated. In some cases more than forty different hydrocarbon species can be detected within the kiln atmosphere. The kiln temperature and oxygen range is also extremely broad. It is difficult to predict the type of combustible vapor that may be present, so an analyzer with a universal response to combustible gases that also can tolerate wide ranges of temperature and oxygen is needed.

NFPA-86 describes the characteristics of analyzers used in the measurement of combustible gases in industrial processes. These include catalytic bead sensor, infrared absorption analyzer (IR), flame temperature analyzer (FTA), and flame ionization detector (FID). It makes clear the need to choose an analyzer with the correct characteristics. The analyzer should be fast, accurate and reliable.

"The choice of the appropriate type depends on factors such as the solvent composition, the need for calibration of more than one solvent, the necessary response time of the measurement system, and the ability to handle factors such as contaminants and oxygen content."

Control Instruments Corporation developed the FTA, or flame temperature analyzer. One embodiment of this analyzer is described in U.S. Pat. No. 5,053,200. It is well suited for flammability measurements under a wide range of conditions. It uses a temperature detector to measure the heat produced by a small "sensing flame." The sensing flame is typically fueled by a small, continuous flow of propane or hydrogen fuel. A sample is extracted from the atmosphere being monitored. The sensing flame sits in a combustion chamber that is completely filled with the sample. A temperature detector is positioned a short distance above the sensing flame, where it can sense the heat produced by the sensing flame. When combustible gases are absent from the sample, the temperature detector receives heat only from fuel combustion: it is at the "zero temperature as in 0% LFL." When combustible gases appear in the sample, they diffuse into the sensing flame, are burned, release heat, and produce a temperature rise in the temperature detector that is directly proportional to the flammability of the sample. The FTA analyzer is calibrated with a gas having a known flammability, so that resulting rise in temperature above the zero temperature, known as the "span temperature," is determined. Following calibration, the flammability of a sample can be calculated from the zero and span temperatures.

A significant advantage of the FTA analyzer is its uniform response to a wide variety of combustible gases and vapors. This is extremely useful when the combustible gases, or their relative proportions in a mixture, are unknown. Experiments have shown that this is achieved through diffusion of combustible gases from the sample into the sensing flame.

One of the few disadvantages of the FTA has been the effect that varying concentrations of oxygen in the sample can have on the zero temperature. The sensing flame requires oxygen from the sample. As the sample's oxygen concentration decreases, the flame begins to starve. It grows larger and changes shape. This in turn produces a false signal, called the oxygen effect, which is equivalent to a shift in the zero temperature of about +1% LFL for every 1% decrease in the sample's oxygen concentration. Below a 10% sample oxygen concentration, the flame begins to destabilize, and the error signal declines somewhat. At about 6% the sensing flame is extinguished, which is called flameout. The FTA oxygen effect is equivalent to a change in zero temperature because it is independent of the concentration of combustible gases in the sample.

An important characteristic of the FTA's sensing flame is its inherently failsafe design. The "zero" temperature of approximately 500° C. disposes the device to readily reveal faults. For example, a failure of flow to the analyzer, such as can occur from a clogged sample tube, will cause flameout from oxygen starvation and produce a significant negative deflection in the measurement circuit that is readily distinguished from valid measurements. A fault signal can therefore signal this condition to prevent mis-interpretation of the analyzer reading. To maintain this failsafe characteristic, the design of the sensing flame must ideally be such that oxygen starvation causes only positive deflections in measurement right up to the point of flameout, at which point a sudden and complete destabilization of the flame, and flameout, occurs. In this way, errors may cause exaggerated readings, but can never under-report the concentration of combustibles.

The accuracy of measurement typically required of a flammability analyzer by industry standards is +/−3% LFL. An improvement to the FTA which would reduce the oxygen effect below this accuracy limit is therefore desirable. Because they both exceed the limit to accuracy, and also underreport the concentration of combustibles, errors more negative than −3% LFL are particularly undesirable.

One attempt by Control Instruments Corporation to improve the FTA is called air dilution. Air dilution is a sample preparation technique, whereby equal amounts of air and sample are mixed together to form an air-sample mixture that is then drawn into the analyzer. By using equal amounts of air and sample, known as a 1:1 air dilution ratio, the air-sample mixture will always contain at least 10% oxygen, which prevents instability and flameout. However, air dilution by itself does not improve the oxygen effect. Even though the magnitude of the oxygen effect is halved, so too is the concentration of combustible gases. So the error from the oxygen effect remains in equal proportion to the flammability signal. The analyzer's indicated reading will still have about the same error, expressed in terms of % LFL. Furthermore, the signal to noise ratio is unfavorably decreased, and the sample preparation apparatus introduces a new source of error. Unintentional variations in the ratio of air to sample can cause significant errors in the measurement.

Due to the limitations given above, air dilution and support air techniques have been used only where absolutely necessary to prevent flameout, but so far have not led to a significant improvement in performance of the analyzer.

Until this time, there has been no satisfactory solution to the oxygen problem in a flame temperature analyzer. However, an apparently similar problem has been solved in a related device, the flame ionization detector, or FID.

The FID is one of the most well known and widely used methods for the analysis of hydrocarbons. It uses an electrometer, a sensitive ammeter, to measure the ion current formed by the combustion of hydrocarbons in a hydrogen flame. The sample is mixed with fuel and is then injected into the burner. The flame sits in a combustion chamber that is filled with pure combustion air. The flame draws oxygen from this combustion air, which is delivered to the combustion chamber at an optimal rate, in order to keep the flame stable with an excess of oxygen at a constant concentration.

A FID that uses pure hydrogen fuel can have a large error, called an oxygen dependency or oxygen synergism, when the oxygen concentration in the sample changes. This error can be equivalent to a span shift of 30 percent or more. The zero is unaffected. One explanation for this behavior is that variations in the sample oxygen concentration can change the rate of ion production in the flame. The solution to oxygen dependency in a FID is the addition of inert gas, such as nitrogen or helium, in the proportion 40% hydrogen to 60% nitrogen or helium. The solution is well known, and is described in the U.S. Environmental Protection Agency's Method 25A for measuring hydrocarbon pollutants with a FID.

For a FID, adding inert gas, for example nitrogen, reduces the oxygen concentration of the hydrogen-nitrogen-sample mixture so that it cannot burn until it is provided with oxygen from the combustion air that surrounds the flame. Thus all the hydrocarbons burn in the outer mantle of the flame and produce ions at a rate that is independent of the oxygen concentration in the sample and only depends on the concentration of hydrocarbons.

If the inert gas is not added to the fuel in a FID, and the concentration of oxygen in the sample can vary, the oxygen concentration of the fuel-sample mixture can sometimes be sufficient to burn as it exits the burner, and at other times insufficient to burn. Ions are produced, and collected as a signal, at a different rate when there is partial burning of the sample as it exists the burner, so signal strength depends on both the concentration of hydrocarbons and on the Concentration of oxygen in the sample.

To one familiar with the FID, it might then seem reasonable to apply this solution to the FTA. However, experiments with hydrogen-nitrogen fuel have shown that the solution to the oxygen problem for the FID is not so useful for a FTA. Hydrogen-nitrogen fuel reduces the FTA oxygen effect only partially, produces an "unsafe" error, and greatly increases fuel costs.

Monitoring a process to prevent fire or explosion is most commonly performed continuously, 24 hours a day, 365 days per year. Compared to pure hydrogen, a hydrogen-nitrogen mixture is more than twice as costly and is consumed at nearly three times the rate. Overall, the hydrogen-nitrogen fuel is several times more expensive to use than pure hydrogen, and requires three times the rate of cylinder changes.

Hydrogen-nitrogen fuel also has the disadvantage of a negative deflection in reading from the oxygen effect. The error produced by changes in oxygen concentration is therefore not failsafe, and so is more undesirable than other types of error.

A method is needed that removes the oxygen effect from the FTA, without requiring a more expensive fuel supply, and without reducing signal strength or otherwise degrading performance.

The present invention solves this problem in two ways. One method is an improvement to air dilution, in which the flame is enriched with fuel. The other method uses air premixed with the fuel to stabilize the flame. Both methods give a significant advantage in performance of the FTA. They can be used alone, or in combination, to produce a FTA with a minimum oxygen effect.

The flame enrichment technique gives better than 50% reduction in oxygen effect without requiring a more expensive fuel, and only at the cost of a somewhat higher rate of fuel consumption. The technique uses a higher rate of fuel flow to establish a flame with a higher initial "zero" temperature than in the typical FTA. When this is done, the flame is about 125° C. hotter in zero conditions. It also is less prone to flameout, and has a lower magnitude of oxygen effects over the entire oxygen range. Its sole benefit that, somewhat surprisingly, makes it useful in the analyzer, is that the majority of the oxygen effect occurs at concentration below 10% by volume oxygen. The upward shift in reading in the range of oxygen between 10% and 20.9% by volume is reduced for this larger flame. Combining the larger flame with air dilution overcomes one of the limitations of the air dilution previously described.

The second method improves the FTA oxygen effect by using a method nearly opposite that of a FID. The FTA oxygen effect is removed by the addition of air to provide both oxygen and nitrogen to the fuel. This surprising outcome arises from significant differences in the principle of operation of the FTA compared to the FID. Although both analyzers use flames, the FID depends upon ion production and the FTA depends upon heat formation. As a consequence, the FID can not measure combustibles gases that produce no ions, such as hydrogen and carbon monoxide, but a FTA can. Furthermore, the FID gives a more or less direct measure of the amount of hydrocarbon in the sample, while the FTA measures the flammability of the sample. For optimal ion production, the FID must have sample premixed with fuel and injected into the burner. For measurement of flammability, the FTA must have the sample diffuse into the flame, and can not have the sample premixed with fuel and injected into the burner.

The oxygen dependency in the FID is removed by ensuring that the burner always has less than approximately 6% oxygen, so that there is never a combustion zone at the tip of the burner, and so that the rate of ion production can not be influenced by the presence, absence, or attenuation of this combustion zone as the sample oxygen concentration changes.

Mixing a small amount of air with the fuel before it is injected into the burner prevents the oxygen effect in a FTA. The amount of air is surprisingly small. It is not enough to fully support combustion of all the fuel—in fact, experiments have shown that too much air, and in particular a stoichiometric concentration, degrades performance. The amount of air needed to remove the oxygen effect from the FTA is that amount which provides just enough oxygen, about 10% by volume, to form a combustion zone deep within the flame at the tip of the burner, and at the same time enough nitrogen from the added air to stabilize the flame by lowering the velocity gradient at the base of the flame. As a result, the oxygen effect is almost completely removed. Most significantly, performance is not otherwise affected. The relatively small amount of added air does not interfere with the diffusion of the sample into the sensing flame. The signal strength and performance of the analyzer are not compromised. Furthermore, because a compressed air supply is already necessary for the operation of the FTA, the addition of air can be easily achieved without requiring the burden or added expense of a special fuel supply.

Hydrogen-oxygen fuel, in addition to the same problem of cost as hydrogen-nitrogen fuel, has the added element of fuel safety concerns. Mixtures of 10% by volume oxygen in hydrogen eliminate approximately half of the undesirable oxygen effect in a FTA. However, this mixture is not safe or legal to store in a compressed gas cylinder. It could be produced by mixing, but would require the significant added expense of an additional oxidant supply system that would, for safety reasons, have to be separate from the hydrogen supply system.

U.S. Pat. No. 3,767,363, Hofman et al, describes a method of removing the oxygen dependence in a FID by the addition of air to the fuel-sample mixture before injecting the combined air-fuel-sample mixture into the burner. Hofman also describes the benefit of using "regular air" as the "compensating gas," in order to avoid the complexity and cost of "synthetic air" from a compressed gas cylinder. At first glance, Hofman would appear to foresee the addition of air to fuel in a FTA analyzer. But under further examination, the mechanism by which Hofman removes the FID oxygen dependency is consistent with that described above for FID fuels made up of nitrogen and hydrogen, or helium and hydrogen. The ratios of hydrogen flow, sample flow, and airflow are such that the oxygen concentration of the total air-fuel-sample mixture that is ultimately delivered to the burner will vary from about 4% oxygen to about 6% oxygen when the sample oxygen concentration varies from 0% to 21%. This is achieved by using a relatively low percentage of sample in the total mixture. One can reason that the widespread use of nitrogen and helium in FID fuel supplies, and not air, is due to the fact that the prevailing method allows three times as much sample to be burned, and thus yields three times as much signal strength, while still keeping the air-fuel-sample mixture to the burner at or below about 6% oxygen, where combustion at the burner tip can not occur.

U.S. Pat. No. 6,096,178, Amirav et al, describes a FID having a hydrogen-oxygen fuel supply from an electrolyzer. The benefit of this design is in greater portability and simplification of the gas management system. Amirav does not disclose the effect that this fuel scheme has on the signal strength, or oxygen dependency, compared to a conventional FID. The ratio of hydrogen to oxygen in the fuel is derived from its origin in the electrolysis of water. When electrolyzed, water releases hydrogen and oxygen in a ratio of two parts by volume hydrogen for every one part by volume oxygen. Amirav uses oxygen and hydrogen, at a combined rate of 23 milliliters per minute, mixed with up to 8 milliliters per minute of sample, for a total of 31 milliliters per minute delivered to the burner. The oxygen-hydrogen-sample mixture to the burner will have a range of oxygen concentrations from a minimum of 24% oxygen to a maximum of 30% oxygen. It is likely that the Amirav device could still have a significant oxygen dependency if it is used to measure a sample having a varying concentration of oxygen.

U.S. Pat. No. 3,984,205, Karas et al, describes a FID that is optimized to have a small flame size and relatively high signal strength by injecting air, fuel, and sample into the burner, and by providing and a minimum of excess combustion air to support the flame. In the Karas device, the problem of oxygen dependency does not arise. The sample contains only hydrocarbon eluted from a chromatographic column using hydrogen, and therefore there is no sample oxygen. The oxygen concentration in the burner is determined completely by the air-fuel ratio, and can be held constant by controlling the proportion of air and fuel. No oxygen effect is discussed, most likely because none is anticipated, because the device is intended for use in a chromatographic column. If the Karas device is adapted for use with a sample in air with varying concentrations of oxygen, then the problem of oxygen dependency would arise.

U.S. Pat. No. 5,432,095, Forsberg, describes a FID that is optimized to give a more uniform response to different hydrocarbons in an "air sample." This is achieved by mixing the sample and fuel in approximately equal proportions and injecting the mixture into the burner, while at the same time using the sample as combustion air to support the flame. The Forsberg device is adapted for use with the so called "air sample" wherein one can anticipate little or no variation in oxygen concentration. The device would certainly exhibit an oxygen dependency if it were used to sample for an atmosphere having varying concentrations of oxygen. In fact, the Forsberg device can be expected to have a greater oxygen dependency than the traditional FID because it uses sample in place of combustion air and so has a dependency from the sample in the burner as well as a dependency from the sample surrounding the flame.

U.S. Pat. No. 4,311,664, Zaremba et al, describes a flame photometric detector in which an arrangement of two nozzles, having fuel, sample and oxidant, can be used to ensure continuity of measurement by the prevention of flameout. It does not address oxygen effects, nor does it optimize performance, but rather keeps the flame lit so that the measuring process is not terminated by a flameout. By providing two burners across which the flame can jump over, a condition normally causing flameout will instead cause jump-over and then, when the condition clears again, jump-over and resumption of measurement without termination. This approach is useful only in the prevention of flameout that would otherwise interrupt the measuring process.

Other prior art patents exist in which gas measurements are made by a flame.

U.S. Pat. No. 2,437,720, Ackley, uses a change in flame temperature of a premixed flame to detect changes in oxygen concentration. The flame however, is a premixed flame, not a diffusion flame. The flame sits in a combustion chamber filled with air. The sample is premixed with fuel and burned in the flame. Changes in the oxygen concentration of the sample influence the flame temperature. The presence of combustible gases in the sample would confound the oxygen measurement.

Although many prior art patents describe various aspects of the improvements of premixed flames for gas measurement, none concerns itself with the use of a diffusion flame for flammability measurements. The premixed flame is useful for the measurement of total hydrocarbons by weight in a gas as in a FID, or for measurement of the heat of combustions as in a calorimeter, but it is not useful for the measurement of flammability. U.S. Pat. No. 2,818,246, Kappel, describes the measurement of heat treating gases. Air is premixed with fuel, which is then converted in a gas generator and burned in a flame. The premixed air is already consumed by the gas generator prior to being burned in the flame. U.S. Pat. No. 3,086,848, Reinecke, and U.S. Pat. No. 5,741,711 Amirav, are for FID analyzers in which fuel and sample are premixed, and the flame sits in a combustion chamber filled with air. Similarly, U.S. Pat. Nos. 4,382,698 and 4,415,278, Szonntagh, and U.S. Pat. No. 5,224,776, Clingman, describe colorimeters having fuel premixed with sample.

Unlike the other premixed flame techniques, the diffusion flame enables a direct measurement of flammability in which the variation in response for various combustible gases is minimized. "Diffusion flames can best be described as the combustion state controlled by mixing phenomena—i.e. the diffusion of fuel into oxidizer, or vice versa—until some flammable mixture ratio is reached" (Glassman, *Combustion* $3^{rd}$ Edition.). For the great majority of combustible gases, at the LFL, this flammable mixture ratio produces a uniform span temperature. This effect cannot be achieved in a premixed flame.

The invention therefore provides a new means to improve the characteristics of a FTA without reducing performance or adding significant cost. In addition, the invention also enables a new method of oxygen measurement that is useful when existing methods don't work well, such as measuring the concentration of oxygen in a process containing combustible gases.

The CENELEC standard EN 50073 describes characteristics of methods for measuring combustible gases. It includes those listed in NFPA-86, and also some methods for oxygen detection, including electrochemical and paramagnetic. Measurement of oxygen using zirconium oxide sensors is also widely used, except in cases where combustible gases can interfere with the oxygen measurement.

Oxygen measurement can help prevent explosions by indicating the oxygen concentration and giving an alarm when the concentration of oxygen is sufficient to support a fire or explosion. The "limiting oxygen concentration" is the concentration of oxygen below which an explosion is not possible. By keeping an industrial process below the limiting oxygen concentration, fires and explosions are prevented. The devices most commonly used to measure oxygen include paramagnetic, electrochemical and zirconium oxide types.

Electrochemical oxygen sensors have a liquid or gelled electrolyte, which reacts to produce an electric current in the presence of oxygen. One limitation of the electrochemical oxygen sensor is that the operating temperature range is not high enough to monitor certain industrial processes without the use of an expensive and potentially error-prone conditioning apparatus.

Zirconium oxide sensors, also known as solid electrochemical sensors, are also well known. They operate at elevated temperatures, and so can often measure directly from industrial processes. One limitation of the zirconium oxide sensor is that its operating temperature is high enough to promote burning of combustible gases on the surface of the sensing element, thus lowering the measured oxygen concentration by the amount of oxygen consumed.

Paramagnetic oxygen analyzers are also well known. They can effectively measure the oxygen concentration in the industrial process, but they cannot make a measurement of the concentration of combustible gases.

Certain industrial processes that employ high temperatures, such as ceramic kilns and metal coating, are heated directly by burners which discharge the products of combustion into the atmosphere to be measured. This can cause the oxygen concentration to vary over a wide range. These processes may also have concentrations of combustible gases that vary significantly over time or throughout the process, so that measurement of both oxygen and combustibles is necessary. It may be advantageous to measure the process to ensure that there is neither sufficient oxygen nor sufficient combustibles to cause an explosion. In a particular process, it might also be necessary to monitor the concentration of combustible gases at one time or place, and to monitor the oxygen concentration at another. Process safety may require the combustible gas concentrations to be below the LFL when the oxygen concentration is above the LOC during one phase of operation, and then it may require the combustible gases to be below the LFL when the oxygen concentration is above the LOC during another phase. For these processes, a gas analyzer that can accurately measure combustible gases in the presence of varying concentrations of oxygen is needed. In addition, a gas analyzer that can accurately measure oxygen in the presence of combustible gases is needed. The gas analyzer must accurately measure a mixture of combustible gases and oxygen, and can give an alarm if there is present both sufficient oxygen and sufficient combustibles to support a fire or explosion.

The invention also allows a new type of oxygen measurement that solves a problem with the prior art techniques of oxygen measurement. The measurement of oxygen concentration in the presence of combustible gases can be achieved by comparing the signal with and without air added to the fuel. Because the oxygen effect in the FTA is relatively independent of the presence of combustible gases, this comparison can yield a measurement of the oxygen concentration that is independent of the presence of combustible gases.

SUMMARY OF THE INVENTION

Briefly described, the invention is a novel Flame Temperature Analyzer (FTA) method and apparatus capable of measuring both the concentration of combustible gases and the concentration of oxygen in a gas sample. In addition, the FTA of this invention significantly reduces the "oxygen effect" error, exhibited by previous FTA's when the oxygen content of the sample is low. The FTA of this invention functions in part by supplying the sensing, diffusion flame with a mixture that includes a fuel and an oxidant.

The addition of an appropriate amount of oxidant to the sensing flame mixture allows the flame to burn with an inner ignition or combustion zone that stabilizes the main reaction zone. As in a conventional FTA, the main reaction zone is where combustion of the flame fuel with the oxidant from the sample occurs as the fuel diffuses into the sample. In the inner combustion zone of the FTA of the present invention, the flame fuel is partially burned with the oxidant supplied to it, before reaching and providing stability to the outer, main reaction zone. As in conventional FTAs, the heat produced by the main reaction zone depends on the amount of combustible gases, including oxidant, in the sample. A temperature detector measures the heat produced by this part of the sensing flame, enabling the concentration of combustible gases to be calculated.

In the FTA of one embodiment of this invention, the oxygen content of the fuel mixture is maintained at around 10% by volume. This ratio of oxygen ensures that the inner ignition zone only burns part of the fuel while pre-heating the remainder of the fuel, thereby providing the main combustion zone with improved stability in low sample oxygen situations.

In the preferred embodiment, a sample is drawn from the atmosphere being monitored, typically by suction from a pump or aspirator. The sample fills the flame cell. The sensing flame is fed by a source of fuel and oxidant through a burner tube. An igniter, typically a spark discharge to the grounded burner, lights the sensing flame. A temperature detector, typically a thermocouple, is positioned directly above the sensing flame. The temperature detector measures the heat produced by the sensing flame. A measuring circuit amplifies and conditions the temperature detector signal into a flammability reading that represents the concentration of oxygen and/or combustibles gases, or both.

In a further embodiment of the invention, the sensing diffusion flame is further stabilized by including a neutral gas in the flame fuel mixture. In one embodiment of the invention, the flame fuel mixture consists of air and hydrogen in nearly equal proportions. This mixture has approximately 10% oxygen, 40% Nitrogen and 50% hydrogen, suitable for creating the inner, partial combustion zone that provides stability to the sensing flame.

In a further embodiment of the invention the flame temperature analyzer is further stabilized by increasing the initial "zero" flame temperature from a usual value of 500° C. to 625° C. in conjunction with air dilution of the sample. The sample : air dilution ratio in the preferred embodiment of this version of the invention is a one-to-one.

In a further embodiment of the invention, the oxygen content of the sample can be determined by monitoring the variation in the sensing flame's temperature as the oxygen content of the flame fuel mixture is varied.

These and other features of the invention will be more fully understood by reference to the following drawings.

BRIEF DESCRIPTION OF THE DRAWINGS

FIGS. 4a-4c are schematic flow diagrams according to the preferred embodiment of the invention.

FIG. 6a-6f are graphs.

FIGS. 7a-7c are schematic representations of flames used in FTA and FID analyzers.

DETAILED DESCRIPTION

During the course of this description, like numbers will be used to identify like elements according to the different views of the invention.

Figure 1:
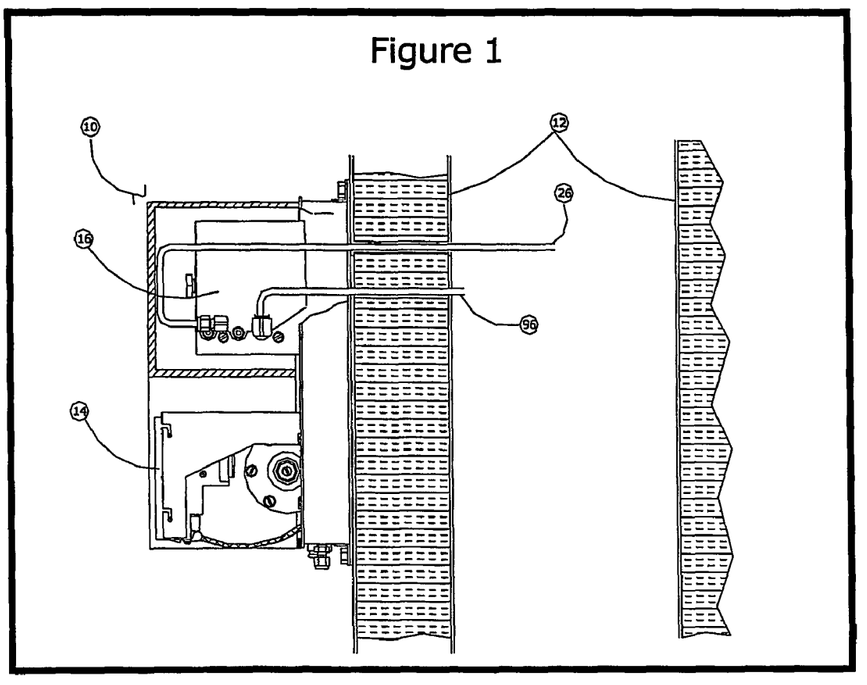
FIG. 1 is a side, elevational, partial cross-sectional view of the analyzer according to the preferred embodiment of the invention.
Figure 2:
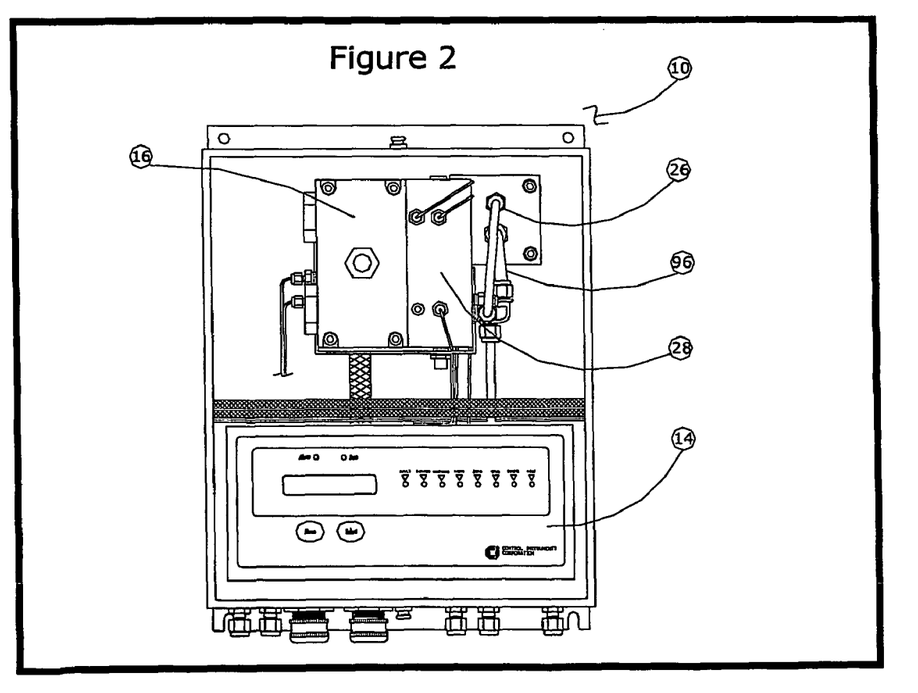
FIG. 2 is a front, elevational, partial cross-sectional view of the analyzer according to the preferred embodiment of the invention.

The preferred embodiment of the invention 10 is illustrated in FIG. 1. The analyzer 10 mounts to the process duct 12 in order to measure the gases therein. The analyzer 10 contains a sample flow system 28, which draws a portion of the gases flowing through process duct 12 through sample tubing 26 into flame cell assembly 16. The gases fill an internal chamber formed by flame cell block 20 and burner plate 18 that contains a sensing flame 48 and temperature detector 52. The heat produced by combustion of these gases in the sensing flame 48 causes an electrical signal in temperature detector 52. The temperature detector 52 is connected to controller 14 by lead wires that carry an electrical signal. This electrical signal is amplified by a measuring circuit 54, converted to a digital signal by an analog to digital converter 76, and conditioned by microprocessor 78 for display as a % LFL reading or % Oxygen reading on a signal meter 84. Microprocessor 78 can compare these readings to pre-programmed alarm settings and generate warning or danger alarms that activate alarm relays 82 which can be used to notify personnel of potentially dangerous conditions, and can be used to automatically and safely stop the process being monitored.

A sample flow system as described in detail in U.S. Pat. No. 5,053,200 can be used to reliably extract a portion of the gases from the process duct 12 and fill the inner chamber of the flame cell assembly 16. Air from compressed air supply 93 passes into the aspirator 94 located within the sample flow system 28 and is ejected through the exhaust tubing 96. Expansion of the compressed air creates suction at the aspirator 94 that causes gases to be drawn from the process duct 12 into the sample tubing 26 through the sample filter 62 and sample flame arrestor 64 into the flame cell, past the sensing flame, and then through the exhaust flame arrestor 66 and exhaust filter 68 and out of the flame cell assembly. The gases then pass through a sample flow orifice 70 and to the aspirator 94 where they are ejected from the aspirator out though the exhaust tubing 96 and back to the process duct 12.

Figure 5:
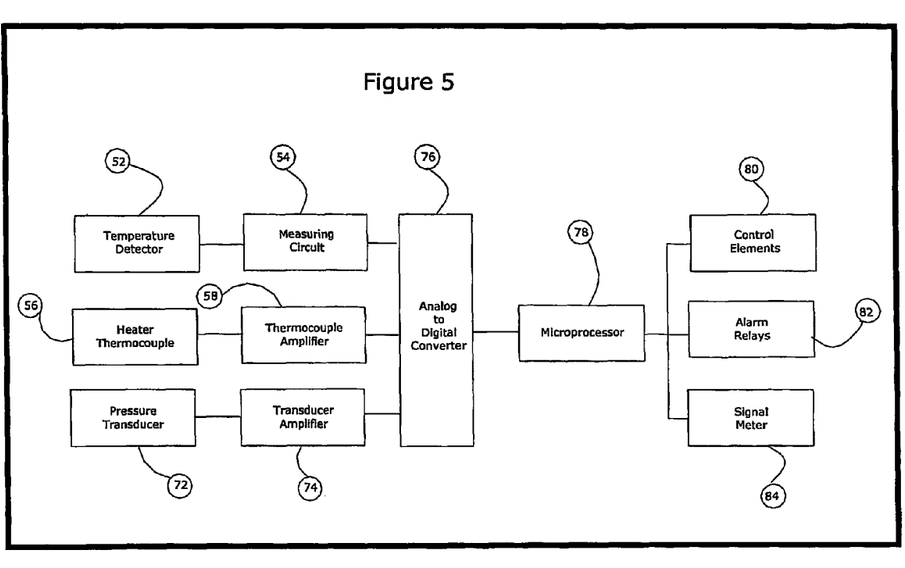
FIG. 5 is a system block diagram according to the preferred embodiment of the invention.

A pressure transducer 72 monitors the pressure drop across sample flow orifice 70. The electrical signal produced by the pressure transducer 72 is amplified by the transducer amplifier 74 located within controller 14, is converted into a digital signal by analog to digital converter 76, and compared by microprocessor 78 to pre-programmed settings that represent a minimum acceptable sample flow rate. If the flow rate falls below the minimum acceptable setting, the microprocessor 78 activates a fault using alarm relays 82 to notify personnel of the fault condition.

Figures 3A, 3B, 3C:
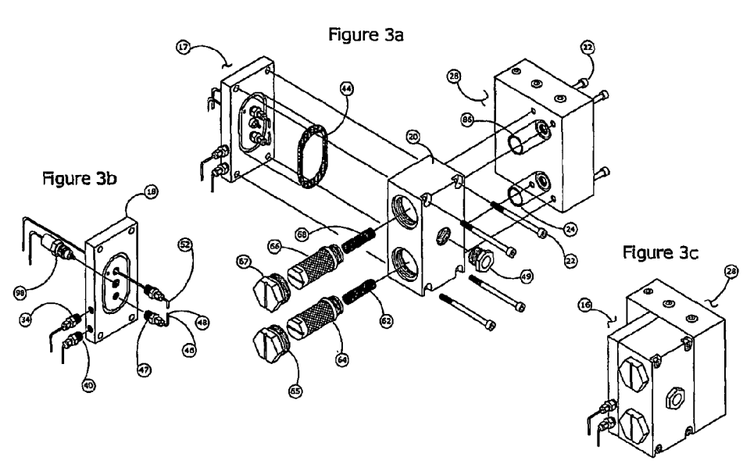
FIGS. 3a-3c are exploded views of the flame cell of the analyzer according to the preferred embodiment of the invention.
Figure 4A:
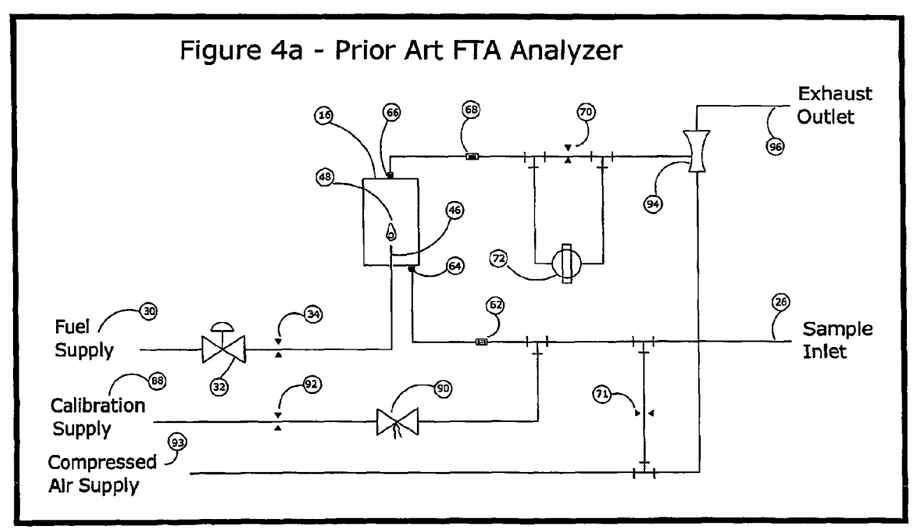
FIG. 4a represents prior art FTA analyzer such as that disclosed under U.S. Pat. No. 5,053,200.
Figure 4B:
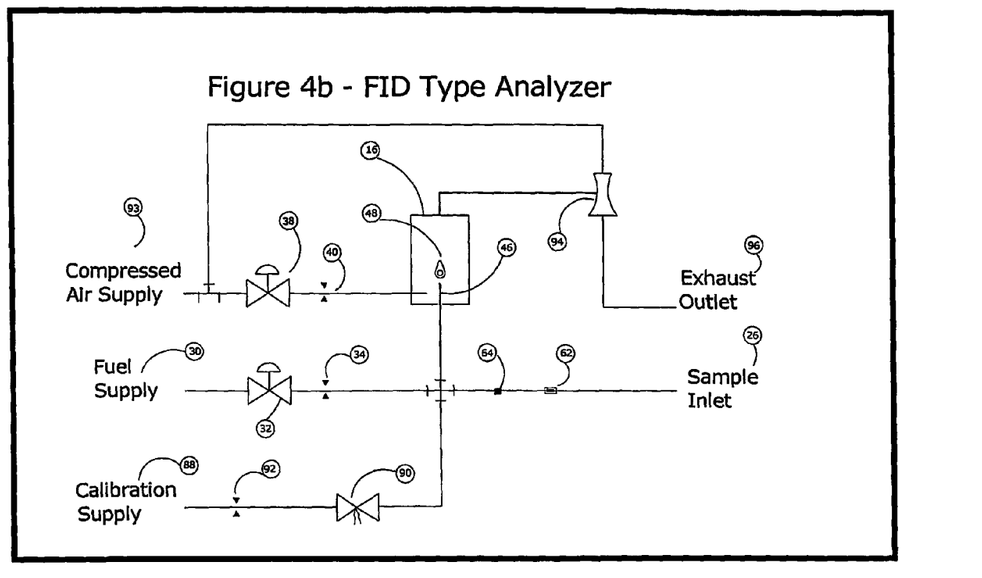
FIG. 4b represents a prior art FID such as in U.S. Pat. No. 3,767,363.
Figure 4C:
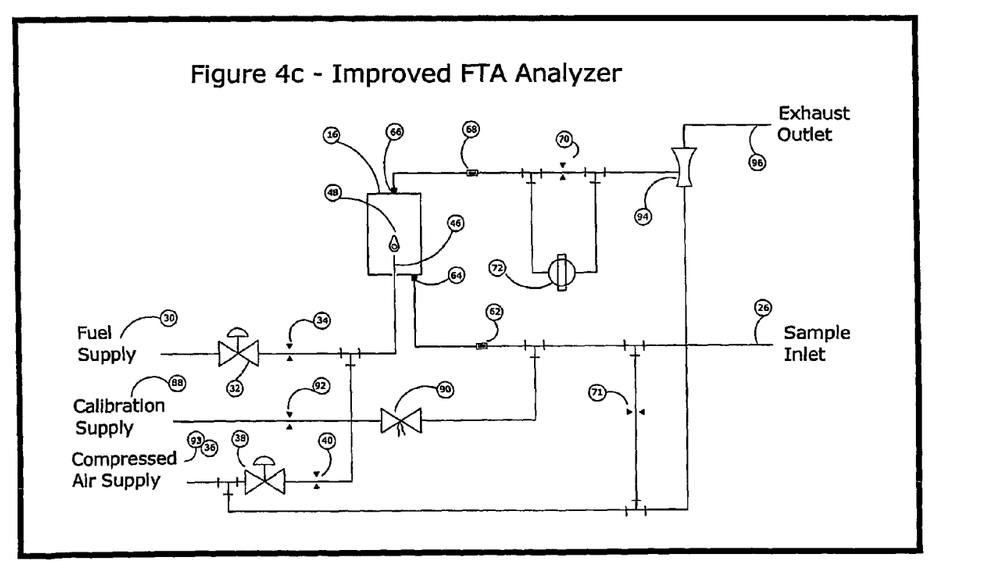
FIG. 4c represents a flame according to the preferred embodiment of the invention.

The flame cell assembly consists of a burner plate assembly 17 attached to a flame cell block 20 by flame cell mounting bolts 22. A burner plate o-ring 44 seals the joint between the burner plate assembly 17 and flame cell block 20 to prevent leaks that might allow sample gases to escape or ambient gases to penetrate the flame cell. The flame cell assembly is likewise mounted to the sample flow system by flame cell mounting bolts 22. The entry for the sample gases and exit for exhaust gases from the flame cell are sealed by the sample inlet o-ring 24 and exhaust o-ring 86 respectively. The sample filter 62 fits inside the sample flame arrestor 64 which screws into the flame cell block 20 and is sealed by a sample flame arrestor cap 65. Likewise the exhaust filter 68 fits inside the exhaust flame arrestor 66 and is sealed by the exhaust flame arrestor cap 67. An observation window 49 is inserted in a threaded hole in the flame cell block 20 to provide the means to observe the sensing flame, or spark ignition, without having to remove the flame cell mounting bolts 22.

The burner plate assembly 17 holds the temperature detector 52 and burner 46. A spark plug 98 passes through the burner plate 18 in the vicinity of the burner 46, and is positioned so that a high voltage can be applied to the spark plug 98 so that it discharges to the burner 46 and ignites the sensing flame 48. Fuel from the fuel supply 30 passes through the fuel pressure control valve 32 and then through the fuel orifice 34 before passing through bored holes in the burner plate 18 and on the to the burner 46. The pressure of the fuel pressure control valve 32 in conjunction with the size of the fuel orifice 34 determines the rate of flow of fuel to the burner 46. Likewise, oxidant, preferably air, from an oxidant supply 36 passes through the oxidant pressure control valve 38 and then through the oxidant orifice 40 before passing through bored holes in the burner plate 18 and on to the burner 46. The pressure of the oxidant pressure control valve 38 in conjunction with the size of the oxidant orifice 40 determines the rate of flow of oxidant to the burner 46.

The measuring circuit conditions the voltage signal from the temperature detector. The temperature of the detector with no combustibles in the sample is known as the "zero." A typical zero temperature is 500 degrees Celsius, measured using a sheathed thermocouple about 1 cm above the flame. The difference between the zero and the temperature of the detector when the sample contains a known concentration of test gas is called the "span." A typical span temperature is approximately 100 degrees Celsius for a 50% LFL mixture, or about 2 degrees Celsius per percent LFL. When the flame cell has a sample of unknown flammability, the measuring circuit can interpolate the reading from the zero and span, and display the flammability of the sample in terms of % LFL. For example, when the zero is 500° C. and the span is 2° C. per % LFL, a temperature of 520° C. would be interpreted as a concentration of 10% LFL in the sample.

By flame temperature, applicants mean the flame temperature as measured. This temperature is not absolute, but depends upon the way in which the thermocouple is positioned relative to the flame. It can for example be the flame temperature as measured by a thermocouple located a short distance above the flame. Alternatively, the flame temperature may be measured by a thermocouple attached to the burner. The important aspect of these experimental temperature measurements is self consistency.

In the preferred embodiment, with the flame temperature measured with a thermocouple above the flame, the zero temperature may be 625 Deg C., whereas with an alternate placement of the thermocouple, for example to the tip of the burner, or perhaps twice the normal distance from the flame, the flame temperature might be lower, or higher, in absolute terms. The optimal performance would still be obtained with the same fuel flow rates and oxygen concentrations, but the absolute temperature measured might be different. Our measurements should not be confused with what combustion engineers refer to as "adiabatic flame temperature" which is a theoretical concept based upon calculation from thermodynamic data.

When the sensing flame is fed pure fuel, an oxygen effect of approximately −2° C. per percent by volume oxygen is observed. For example, if the zero reading is 500° C. with air (20.9% by volume oxygen), when the oxygen concentration of the sample decreased by 10% by volume oxygen, the temperature increases to 520° C. The oxygen effect of +20° C. is equivalent to +10% LFL. Oxygen effects as high as +15% LFL can be observed. With the addition of oxidant to the fuel, the oxygen effect is greatly reduced, and the oxygen effect, over the entire range of oxygen concentrations that will still support the sensing flame, can be held to less than 3% LFL.

FIGS. 6a through 6f are graphs of the oxygen effect in a FTA analyzer for various fuel types. In these graphs, the independent variable is the oxygen concentration in the sample, which was varied from 20.9 percent by volume, the normal atmospheric concentration, down to the point of flameout, where the sensing flame could no longer be sustained. The dependent variable is the analyzer's flammability reading.

Figure 6A:
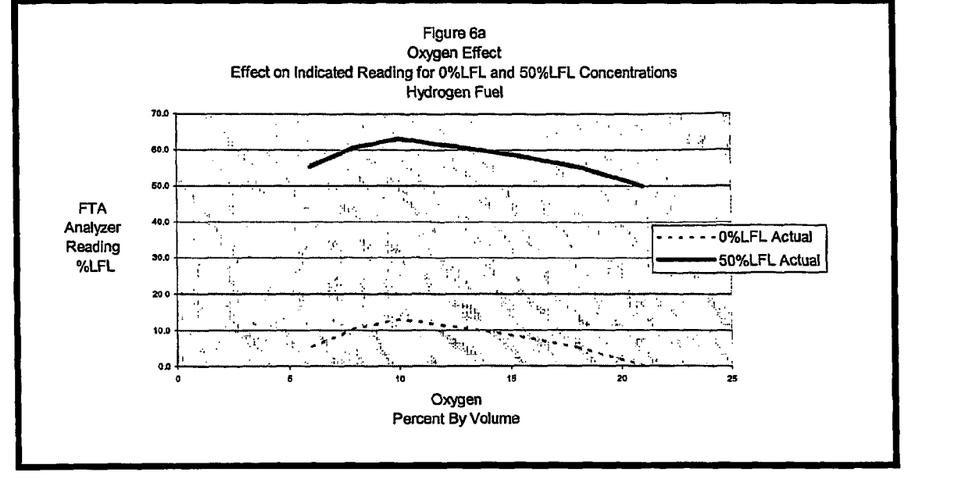

FIG. 6a shows the oxygen effect on the zero reading, and also on the span reading, for the prior art FTA analyzer.

Figure 6B:
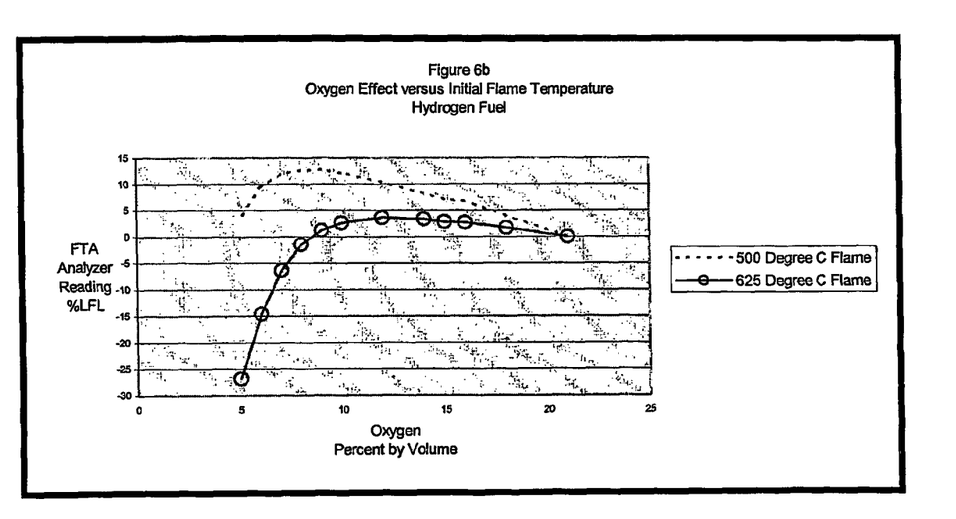

FIG. 6b shows the oxygen effect on the zero reading for a FTA analyzer for an initial zero flame temperature of 500° C., and also for an initial zero flame temperature of 625° C. Both flames remain lit down to about 5% by volume oxygen. The 500° C. flame has a maximum zero effect of about +12% LFL and exhibits no negative readings. The 625° C. flame has a maximum zero effect of about −27% LFL, with most of the zero effect occurring below 10% by volume oxygen.

Figure 6C:
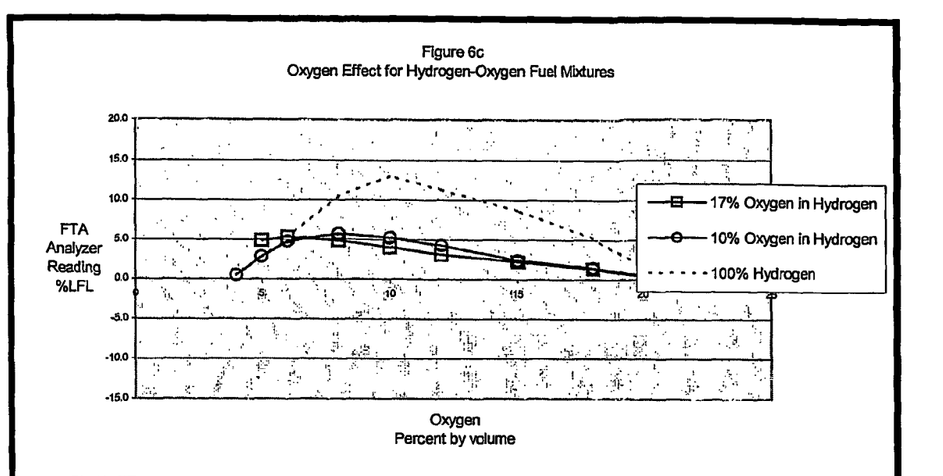

FIG. 6c shows the oxygen effect for several hydrogen-oxygen fuel mixtures. The oxygen effect for pure (100%)

hydrogen fuel is also shown for reference. Hydrogen-oxygen fuel mixtures exhibit less than half the oxygen effect compared to pure hydrogen.

Figure 6D:
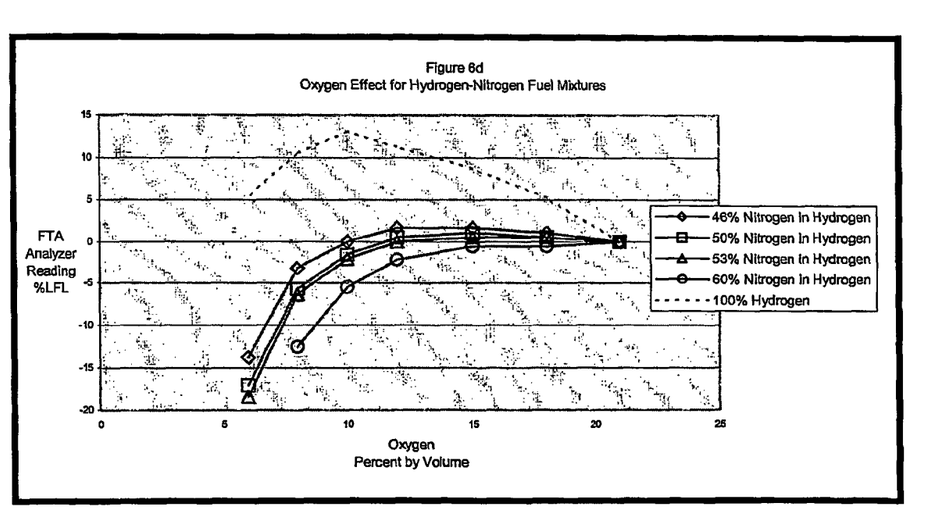

FIG. 6d shows the oxygen effect for several hydrogen-nitrogen mixtures. The oxygen effect for pure (100%) hydrogen fuel is also shown for reference. The hydrogen-nitrogen fuels exhibit a significant zero effect which includes undesirable negative readings.

Figure 6E:
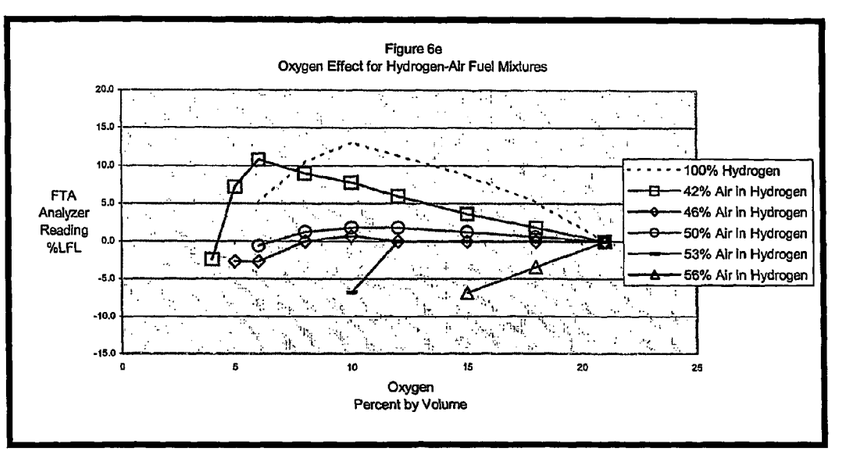

FIG. 6e shows the oxygen effect for several hydrogen-air fuel mixtures. Hydrogen-air fuels of 46% Air to 50% Air have greatly reduced oxygen effect and only slight negative readings.

Figure 6F:
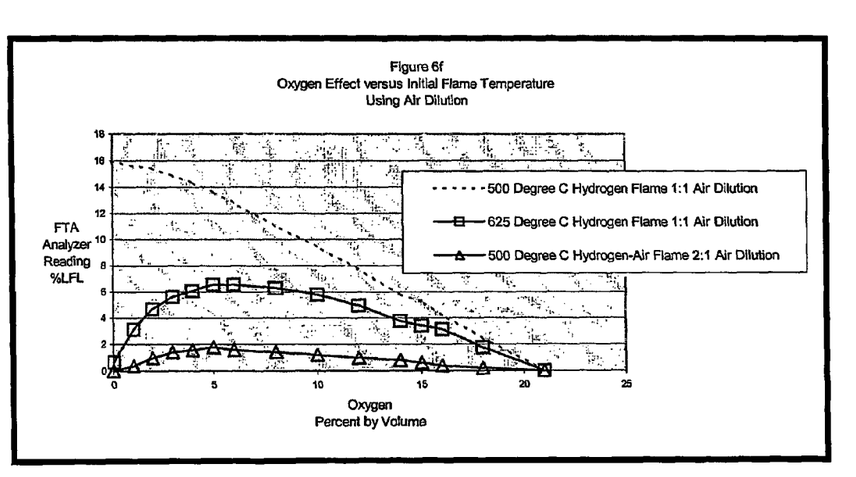

FIG. 6f shows the use of improved fuel types to improve the performance of air dilution. The oxygen effect, when air dilution in a 1:1 ratio of air to sample is used to allow operation down to 0% by volume oxygen, is, for the 625° C. hydrogen flame, less than half that of the 500° C. hydrogen flame. The use of hydrogen-air fuel, with an air dilution in a 2:1 ratio of sample to air, allows operation down to 0% oxygen with a maximum error less than 3% LFL. The improved analyzer can operate down to 0% by volume oxygen without flameout and without negative readings.

Figure 6G:
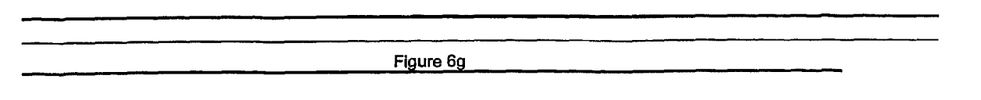
FIG. 6g is a table, of the FTA analyzer reading versus sample oxygen concentration for various fuels.
Figure 7A:
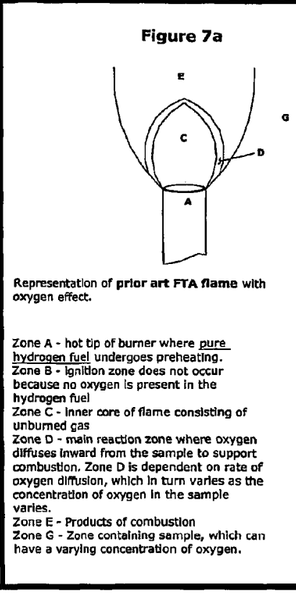
FIG. 7a represents the flame in a prior art FTA analyzer such as that disclosed under U.S. Pat. No. 5,053,200.
Figure 7B:
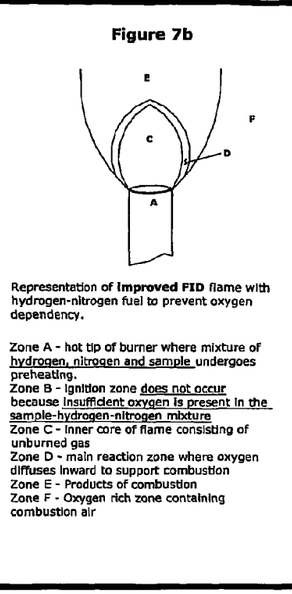
FIG. 7b represents a prior art FID such as in U.S. Pat. No. 3,767,363.
Figure 7C:
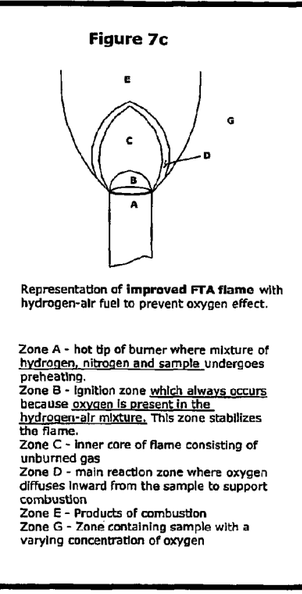
FIG. 7c represents a flame according to the preferred embodiment of the invention.

FIG. 6g is a table that shows both the oxygen effect at 10% oxygen, and the change in signal strength, for a series of different initial flame temperatures.

If measurements are made with oxidant and without, the two measurements can be compared to one another, and the oxygen concentration can be derived. This allows the sensing flame to make oxygen measurements independent of the concentration of combustibles, and combustible measurements independent of the concentration of oxygen.

The pressure of the oxidant pressure control valve 38 may be varied by means of control elements 80 attached to microprocessor 78, so that the oxidant flow rate can be varied in order to determine the concentration of oxygen in the sample gases.

The invention therefore provides a method for measuring the concentration of combustible gas and the concentration of oxygen in a mixture, whereby a temperature detector measures the heat produced by a sensing flame that is formed by a mixture of fuel and an oxidant emitted from a burner.

Special Features Of The Invention.

The oxidant can be air from a compressed air supply, or oxygen from a compressed oxygen cylinder. The oxidant may also be a mixture of air or oxygen and an inert gas such as nitrogen, argon, helium or the like. The concentration of oxidant must be sufficient to create a stable combustion zone in the vicinity of the burner tip. For oxygen, this concentration is optimally 10% by volume oxygen. The range from approximately 9.4% to 10.5% by volume oxygen gives good results. The system which delivers oxygen to the burner may therefore be designed to deliver 10% by volume oxygen, and in so doing, will allow a tolerance of +/−0.5% by volume oxygen without a degradation in performance. A fuel-air mixture of 45% to 50% by volume air in hydrogen will give good results.

The flow of hydrogen fuel can be increased in order to obtain an initial zero flame temperature of 625° C. This enhanced flame size, in conjunction with an air dilution ratio of 1 part air to 1 part sample, will reduce the oxygen effect to approximately 6% LFL over the range from 0 to 20.9% by volume oxygen in the sample.

The 625° C. flame with 1:1 air dilution can be zero calibrated using, in place of air, 15% by volume oxygen in nitrogen. This calibration will result in an offset of about 3% LFL, and will alter the analyzer readings to be within +/−3% LFL over the range from 0 to 20.9% by volume oxygen, thereby making the analyzer conform to the requirement of industry standard accuracy over the entire range of foreseeable oxygen concentrations.

The temperature detector can be a thermocouple, a resistance temperature detector (RTD), or any similar device, including an array of thermocouples.

The temperature detector can be positioned in the exhaust flow of the sensing flame, or it may be attached directly to the tip of the burner, or within the burner in the vicinity of the sensing flame but not in direct contact with the wall of the burner.

The flow rates of fuel and oxidant can be held constant throughout, in order to give a measurement of the flammability of combustible gases without interference from the concentration of oxygen.

The flow rates of oxidant can be turned on and off in order to give a measurement of the flammability of combustible gases in the sample and also the concentration of oxygen in the sample.

The oxidant pressure regulator may be a mass flow controller that is continuously adjusted by the microprocessor.

The burner and detector may be micro-machined in order to optimize the size of the device.

The invention may be used in conjunction with prior art techniques of air dilution and the like, to improve the effectiveness of those techniques.

While the invention has been described with reference to the preferred embodiment thereof it will be appreciated by those of ordinary skill in the art that modifications can be made to parts that comprise the invention without departing from the spirit and scope thereof.

What is claimed is:

1. A gas analyzing method, comprising:
   a) filling a flame cell with a sample gas;
   b) injecting a mixture into said flame cell,
      said mixture including a fuel and an oxidant present in proportions such that burning said mixture creates a diffusion flame comprising an inner ignition zone and a main reaction zone;
   c) measuring a temperature of said diffusion flame; and
   d) calculating a concentration of combustible gases contained in said sample of gas using said temperature.

2. The method of claim 1 wherein said mixture further includes a substantially neutral gas.

3. The method of claim 2 where in said fuel is hydrogen, said oxidant is oxygen and said substantially neutral gas is nitrogen.

4. The method of claim 3 wherein said oxygen content of said mixture is in the range of 9.4% to 10.5%.

5. The method of claim 1, further comprising:
   e) injecting a second mixture into said flame cell, said second mixture including said fuel, and burning said second mixture, thereby creating a second diffusion flame having a main reaction zone and being incapable of supporting an inner ignition zone;
   f) measuring a second temperature of said second diffusion flame;
   g) calculating a concentration of oxygen in said sample, said calculating including comparing said temperature and said second temperature.

6. A gas analyzing apparatus, comprising:
   a flame cell;
   a filling means for filling said flame cell with a gas sample;
   a flammable mixture, said mixture including a fuel and an oxidant;
   an injection means for injecting said mixture into said flame cell;

a burning means for burning said mixture inside said gas sample filled flame cell, thereby creating a diffusion flame including a main reaction zone wherein said gas sample diffuses into said diffusion flame and an inner ignition zone free of said gas sample;

a measuring means for measuring a temperature of said diffusion flame; and a combustible gas concentration calculating means, operatively connected to said measuring means and capable of using said temperature for determining a concentration of combustible gases in said gas sample.

7. The gas analyzing apparatus of claim 6 wherein said mixture further includes a substantially neutral gas.

8. The gas analyzing apparatus of claim 7 wherein said fuel is hydrogen, said oxidant is oxygen and said neutral gas is nitrogen.

9. The gas analyzing apparatus of claim 8 wherein said oxygen content of said mixture is in the range of 9.4% to 10.5%.

10. The gas analyzing apparatus of claim 6, further including:
   a second mixture, said second mixture including said fuel;
   a second diffusion flame created by using said burning means to burn said second mixture, said second diffusion flame having a main reaction zone and being incapable of supporting an inner ignition zone;
   a second temperature of said second diffusion flame obtained using said measuring means;
   an oxygen concentration calculating means, functionally connected to said measuring means and adapted to calculate a concentration of oxygen in said sample by comparing said second temperature with said temperature.

11. A gas analyzing device, comprising:
   a flame cell filled with a gas sample;
   a burner tube having a first and a second end, said first end being located inside said gas filled flame cell, and said burner tube being supplied via said second end with a mixture including a fuel and an oxidant;
   a diffusion flame created inside said flame cell by burning said mixture at said first end of said burner within said gas sample filled flame cell, said diffusion flame having a main reaction zone wherein said gas sample diffuses into said diffusion flame and an inner ignition zone free of said gas sample;
   a temperature sensor located near said diffusion flame capable of providing a temperature of said diffusion flame,
   a calculator, operatively connected to said temperature sensor, and capable of using said temperature to determine a concentration of combustible gases contained in said sample.

12. The gas analyzing device of claim 11 wherein said mixture further includes a substantially neutral gas.

13. The gas analyzing device of claim 12 wherein said fuel is hydrogen, said oxidant is oxygen and said neutral gas is nitrogen.

14. The gas analyzing device of claim 13 wherein said oxygen content of said mixture is in the range of 9.4% to 10.5%.

* * * * *